United States Patent
Sabesan

(10) Patent No.: US 10,448,839 B2
(45) Date of Patent: Oct. 22, 2019

(54) METHODS, SYSTEMS AND APPARATUSES FOR DETECTING INCREASED RISK OF SUDDEN DEATH

(75) Inventor: Shivkumar Sabesan, Houston, TX (US)

(73) Assignee: LivaNova USA, Inc., Houston, TX (US)

( * ) Notice: Subject to any disclaimer, the term of this patent is extended or adjusted under 35 U.S.C. 154(b) by 1338 days.

(21) Appl. No.: 13/453,746

(22) Filed: Apr. 23, 2012

(65) Prior Publication Data

US 2013/0281797 A1    Oct. 24, 2013

(51) Int. Cl.
*A61B 5/0476* (2006.01)
*A61B 5/0205* (2006.01)
(Continued)

(52) U.S. Cl.
CPC .......... *A61B 5/0205* (2013.01); *A61B 5/0402* (2013.01); *A61B 5/0476* (2013.01); *A61B 5/0816* (2013.01); *A61B 5/4094* (2013.01); *G16H 20/17* (2018.01); *G16H 20/30* (2018.01); *G16H 40/63* (2018.01); *G16H 40/67* (2018.01); *G16H 50/20* (2018.01); *A61B 5/1112* (2013.01); *A61B 5/7275* (2013.01); *A61B 5/746* (2013.01); *A61B 5/7465* (2013.01); *A61B 2505/07* (2013.01)

(58) Field of Classification Search
None
See application file for complete search history.

(56) References Cited

U.S. PATENT DOCUMENTS

| | | |
|---|---|---|
| 4,172,459 A | 10/1979 | Hepp |
| 4,197,856 A | 4/1980 | Northrop |

(Continued)

FOREIGN PATENT DOCUMENTS

| | | |
|---|---|---|
| EP | 0944411 B1 | 4/2001 |
| EP | 1145736 A2 | 10/2001 |

(Continued)

OTHER PUBLICATIONS

"Heart rate variability: Standards of measurement, physiological interpretation and clinical use", Task Force of the European Society of Cardiology and the North American Society of Pacing and Electrophysiology, Circulation, Mar. 1993, vol. 93, No. 5, pp. 1043-1065.

(Continued)

*Primary Examiner* — Rex R Holmes
*Assistant Examiner* — Nathan A Baldwin
(74) *Attorney, Agent, or Firm* — Foley & Lardner LLP

(57) ABSTRACT

Methods, systems, and apparatuses for detecting seizure events are disclosed, including a system for identification of an increased risk of a severe neurological event. The system may include an electroencephalogram ("EEG") monitoring unit configured to collect EEG data from the patient during at least a postictal phase of one or more seizures and a processing unit configured to receive the EEG data from the EEG monitoring unit. The processing unit is configured to detect postictal EEG suppression from the EEG data and to identify the increased risk of the severe neurological event based on the detected postictal EEG suppression. Other embodiments are described and claimed.

13 Claims, 4 Drawing Sheets

(51) Int. Cl.
*A61B 5/0402* (2006.01)
*A61B 5/08* (2006.01)
*A61B 5/00* (2006.01)
*G16H 50/20* (2018.01)
*G16H 40/63* (2018.01)
*G16H 40/67* (2018.01)
*G16H 20/30* (2018.01)
*G16H 20/17* (2018.01)
*A61B 5/11* (2006.01)

(56) References Cited

U.S. PATENT DOCUMENTS

| | | |
|---|---|---|
| 4,291,699 A | 9/1981 | Geddes et al. |
| 4,295,474 A | 10/1981 | Fischell |
| 4,320,766 A | 3/1982 | Alihanka et al. |
| 4,541,432 A | 9/1985 | Molina-Negro et al. |
| 4,573,481 A | 3/1986 | Bullara |
| 4,702,254 A | 10/1987 | Zabara |
| 4,867,164 A | 9/1989 | Zabara |
| 4,920,979 A | 5/1990 | Bullara |
| 4,949,721 A | 8/1990 | Toriu et al. |
| 4,979,511 A | 12/1990 | Terry, Jr. |
| 5,025,807 A | 6/1991 | Zabara |
| 5,062,169 A | 11/1991 | Kennedy et al. |
| 5,113,869 A | 5/1992 | Nappholz et al. |
| 5,137,020 A | 8/1992 | Wayne et al. |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,194,847 A | 3/1993 | Taylor et al. |
| 5,203,326 A | 4/1993 | Collins |
| 5,205,285 A | 4/1993 | Baker, Jr. |
| 5,213,568 A | 5/1993 | Lattin et al. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,243,980 A | 9/1993 | Mehra |
| 5,251,634 A | 10/1993 | Weinberg |
| 5,263,480 A | 11/1993 | Wernicke et al. |
| 5,269,302 A | 12/1993 | Swartz et al. |
| 5,299,569 A | 4/1994 | Wernicke et al. |
| 5,304,206 A | 4/1994 | Baker, Jr. et al. |
| 5,307,263 A | 4/1994 | Brown |
| 5,313,953 A | 5/1994 | Yomtov et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,357,427 A | 10/1994 | Langen et al. |
| 5,404,877 A | 4/1995 | Nolan et al. |
| 5,425,373 A | 6/1995 | Causey, III |
| 5,441,047 A | 8/1995 | David et al. |
| 5,513,649 A | 5/1996 | Gevins et al. |
| 5,522,862 A | 6/1996 | Testerman et al. |
| 5,523,742 A | 6/1996 | Simkins et al. |
| 5,531,778 A | 7/1996 | Maschino et al. |
| 5,540,730 A | 7/1996 | Terry, Jr. et al. |
| 5,540,734 A | 7/1996 | Zabara |
| 5,544,649 A | 8/1996 | David et al. |
| 5,544,661 A | 8/1996 | Davis et al. |
| 5,553,609 A | 9/1996 | Chen et al. |
| 5,571,150 A | 11/1996 | Wernicke et al. |
| 5,601,435 A | 2/1997 | Quy |
| 5,610,590 A | 3/1997 | Johnson et al. |
| 5,611,350 A | 3/1997 | John |
| 5,645,077 A | 7/1997 | Foxlin |
| 5,645,570 A | 7/1997 | Corbucci |
| 5,651,378 A | 7/1997 | Matheny et al. |
| 5,658,318 A | 8/1997 | Stroetmann et al. |
| 5,683,422 A | 11/1997 | Rise |
| 5,690,681 A | 11/1997 | Geddes et al. |
| 5,690,688 A | 11/1997 | Noren et al. |
| 5,700,282 A | 12/1997 | Zabara |
| 5,707,400 A | 1/1998 | Terry, Jr. et al. |
| 5,716,377 A | 2/1998 | Rise et al. |
| 5,720,771 A | 2/1998 | Snell |
| 5,722,999 A | 3/1998 | Snell |
| 5,743,860 A | 4/1998 | Hively et al. |
| 5,748,113 A | 5/1998 | Torch |
| 5,759,199 A | 6/1998 | Snell et al. |
| 5,792,186 A | 8/1998 | Rise |
| 5,800,474 A | 9/1998 | Benabid et al. |
| 5,807,284 A | 9/1998 | Foxlin |
| 5,808,552 A | 9/1998 | Wiley et al. |
| 5,833,709 A | 11/1998 | Rise et al. |
| 5,853,005 A | 12/1998 | Scanlon |
| 5,879,309 A | 3/1999 | Johnson et al. |
| 5,905,436 A | 5/1999 | Dwight et al. |
| 5,913,876 A | 6/1999 | Taylor et al. |
| 5,916,181 A | 6/1999 | Socci et al. |
| 5,916,239 A | 6/1999 | Geddes et al. |
| 5,928,272 A | 7/1999 | Adkins et al. |
| 5,941,906 A | 8/1999 | Barreras, Sr. et al. |
| 5,942,979 A | 8/1999 | Luppino |
| 5,978,702 A | 11/1999 | Ward et al. |
| 5,978,972 A | 11/1999 | Stewart et al. |
| 5,987,352 A | 11/1999 | Klein et al. |
| 5,995,868 A | 11/1999 | Dorfmeister et al. |
| 6,016,449 A | 1/2000 | Fischell et al. |
| 6,018,682 A | 1/2000 | Rise |
| 6,048,324 A | 4/2000 | Socci et al. |
| 6,061,593 A | 5/2000 | Fischell et al. |
| 6,073,048 A | 6/2000 | Kieval et al. |
| 6,083,249 A | 7/2000 | Familoni |
| 6,091,992 A | 7/2000 | Bourgeois et al. |
| 6,095,991 A | 8/2000 | Krausman et al. |
| 6,104,956 A | 8/2000 | Naritoku et al. |
| 6,115,628 A | 9/2000 | Stadler et al. |
| 6,115,630 A | 9/2000 | Stadler et al. |
| 6,128,538 A | 10/2000 | Fischell et al. |
| 6,134,474 A | 10/2000 | Fischell et al. |
| 6,162,191 A | 12/2000 | Foxlin |
| 6,163,281 A | 12/2000 | Torch |
| 6,167,311 A | 12/2000 | Rezai |
| 6,171,239 B1 | 1/2001 | Humphrey |
| 6,175,764 B1 | 1/2001 | Loeb et al. |
| 6,200,331 B1 * | 3/2001 | Swartz .............. A61N 1/08 607/1 |
| 6,205,359 B1 | 3/2001 | Boveja |
| 6,208,894 B1 | 3/2001 | Schulman et al. |
| 6,208,902 B1 | 3/2001 | Boveja |
| 6,221,908 B1 | 4/2001 | Kilgard et al. |
| 6,246,344 B1 | 6/2001 | Torch |
| 6,248,080 B1 | 6/2001 | Miesel et al. |
| 6,253,109 B1 | 6/2001 | Gielen |
| 6,264,614 B1 | 7/2001 | Albert et al. |
| 6,269,270 B1 | 7/2001 | Boveja |
| 6,272,379 B1 | 8/2001 | Fischell et al. |
| 6,304,775 B1 | 10/2001 | Iasemidis et al. |
| 6,315,740 B1 | 11/2001 | Singh |
| 6,324,421 B1 | 11/2001 | Stadler et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,784 B1 | 3/2002 | Lozano et al. |
| 6,356,788 B2 | 3/2002 | Boveja |
| 6,358,203 B2 | 3/2002 | Bardy |
| 6,361,507 B1 | 3/2002 | Foxlin |
| 6,361,508 B1 | 3/2002 | Johnson et al. |
| 6,366,813 B1 | 4/2002 | DiLorenzo |
| 6,366,814 B1 | 4/2002 | Boveja et al. |
| 6,374,140 B1 | 4/2002 | Rise |
| 6,397,100 B2 | 5/2002 | Stadler et al. |
| 6,427,086 B1 | 7/2002 | Fischell et al. |
| 6,429,217 B1 | 8/2002 | Puskas |
| 6,441,731 B1 | 8/2002 | Hess |
| 6,449,512 B1 | 9/2002 | Boveja |
| 6,459,936 B2 | 10/2002 | Fischell et al. |
| 6,463,328 B1 | 10/2002 | John |

(56) References Cited

U.S. PATENT DOCUMENTS

| | | |
|---|---|---|
| 6,466,822 B1 | 10/2002 | Pless |
| 6,473,639 B1 | 10/2002 | Fischell et al. |
| 6,473,644 B1 | 10/2002 | Terry, Jr. et al. |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,497,655 B1 | 12/2002 | Linberg et al. |
| 6,501,983 B1 | 12/2002 | Natarajan et al. |
| 6,505,074 B2 | 1/2003 | Boveja et al. |
| 6,532,388 B1 | 3/2003 | Hill et al. |
| 6,539,263 B1 | 3/2003 | Schiff et al. |
| 6,542,081 B2 | 4/2003 | Torch |
| 6,542,774 B2 | 4/2003 | Hill et al. |
| 6,549,804 B1 | 4/2003 | Osorio et al. |
| 6,556,868 B2 | 4/2003 | Naritoku et al. |
| 6,560,486 B1 | 5/2003 | Osorio et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,594,524 B2 | 7/2003 | Esteller et al. |
| 6,599,250 B2 | 7/2003 | Webb et al. |
| 6,600,956 B2 | 7/2003 | Maschino et al. |
| 6,609,025 B2 | 8/2003 | Barrett et al. |
| 6,610,713 B2 | 8/2003 | Tracey |
| 6,611,715 B1 | 8/2003 | Boveja |
| 6,611,783 B2 | 8/2003 | Kelly, Jr. et al. |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,985 B2 | 9/2003 | Sweeney et al. |
| 6,628,987 B1 | 9/2003 | Hill et al. |
| 6,629,990 B2 | 10/2003 | Putz et al. |
| 6,647,296 B2 | 11/2003 | Fischell et al. |
| 6,656,125 B2 | 12/2003 | Misczynski et al. |
| 6,656,960 B2 | 12/2003 | Puskas |
| 6,668,191 B1 | 12/2003 | Boveja |
| 6,671,555 B2 | 12/2003 | Gielen et al. |
| 6,671,556 B2 | 12/2003 | Osorio et al. |
| 6,684,105 B2 | 1/2004 | Cohen et al. |
| 6,721,603 B2 | 4/2004 | Zabara et al. |
| 6,730,047 B2 | 5/2004 | Socci et al. |
| 6,731,979 B2 | 5/2004 | MacDonald |
| 6,735,474 B1 | 5/2004 | Loeb et al. |
| 6,738,671 B2 | 5/2004 | Christophersom et al. |
| 6,760,626 B1 | 7/2004 | Boveja |
| 6,763,256 B2 | 7/2004 | Kimball et al. |
| 6,768,969 B1 | 7/2004 | Nikitin et al. |
| 6,786,877 B2 | 9/2004 | Foxlin |
| 6,788,975 B1 | 9/2004 | Whitehurst et al. |
| 6,793,670 B2 | 9/2004 | Osorio et al. |
| 6,819,953 B2 | 11/2004 | Yonce et al. |
| 6,819,956 B2 | 11/2004 | DiLorenzo |
| 6,832,114 B1 | 12/2004 | Whitehurst et al. |
| 6,836,685 B1 | 12/2004 | Fitz |
| 6,850,601 B2 | 2/2005 | Jones, III et al. |
| 6,879,850 B2 | 4/2005 | Kimball |
| 6,885,888 B2 | 4/2005 | Rezai |
| 6,904,390 B2 | 6/2005 | Nikitin et al. |
| 6,920,357 B2 | 7/2005 | Osorio et al. |
| 6,923,784 B2 | 8/2005 | Stein |
| 6,931,274 B2 | 8/2005 | Williams |
| 6,934,580 B1 | 8/2005 | Osorio et al. |
| 6,934,585 B1 | 8/2005 | Schloss et al. |
| 6,944,501 B1 | 9/2005 | Pless |
| 6,957,107 B2 | 10/2005 | Rogers et al. |
| 6,959,215 B2 | 10/2005 | Gliner et al. |
| 6,961,618 B2 | 11/2005 | Osorio et al. |
| 6,976,958 B2 | 12/2005 | Quy |
| 6,984,993 B2 | 1/2006 | Ariav |
| 6,985,771 B2 | 1/2006 | Fischell et al. |
| 6,990,377 B2 | 1/2006 | Gliner et al. |
| 7,006,859 B1 | 2/2006 | Osorio et al. |
| 7,006,872 B2 | 2/2006 | Gielen et al. |
| 7,010,351 B2 | 3/2006 | Firlik et al. |
| 7,024,247 B2 | 4/2006 | Gliner et al. |
| 7,035,684 B2 | 4/2006 | Lee |
| 7,043,305 B2 | 5/2006 | KenKnight et al. |
| 7,047,074 B2 | 5/2006 | Connelly et al. |
| 7,054,686 B2 | 5/2006 | MacDonald |
| 7,054,792 B2 | 5/2006 | Frei et al. |
| 7,058,453 B2 | 6/2006 | Nelson et al. |
| 7,068,842 B2 | 6/2006 | Liang et al. |
| 7,076,288 B2 | 7/2006 | Skinner |
| 7,077,810 B2 | 7/2006 | Lange et al. |
| 7,079,977 B2 | 7/2006 | Osorio et al. |
| 7,089,059 B1 | 8/2006 | Pless |
| 7,104,947 B2 | 9/2006 | Riehl |
| 7,110,820 B2 | 9/2006 | Tcheng et al. |
| 7,112,319 B2 | 9/2006 | Broderick et al. |
| 7,127,370 B2 | 10/2006 | Kelly, Jr. et al. |
| 7,134,996 B2 | 11/2006 | Bardy |
| 7,139,677 B2 | 11/2006 | Hively |
| 7,146,211 B2 | 12/2006 | Frei et al. |
| 7,146,217 B2 | 12/2006 | Firlik et al. |
| 7,146,218 B2 | 12/2006 | Esteller et al. |
| 7,149,572 B2 | 12/2006 | Frei et al. |
| 7,156,808 B2 | 1/2007 | Quy |
| 7,156,809 B2 | 1/2007 | Quy |
| 7,164,941 B2 | 1/2007 | Misczynski et al. |
| 7,167,743 B2 | 1/2007 | Heruth et al. |
| 7,167,750 B2 | 1/2007 | Knudson et al. |
| 7,174,206 B2 | 2/2007 | Frei et al. |
| 7,177,678 B1 | 2/2007 | Osorio et al. |
| 7,188,053 B2 | 3/2007 | Nikitin et al. |
| RE39,539 E | 4/2007 | Torch |
| 7,204,833 B1 | 4/2007 | Osorio et al. |
| 7,209,786 B2 | 4/2007 | Brockway et al. |
| 7,209,787 B2 | 4/2007 | DiLorenzo |
| 7,221,981 B2 | 5/2007 | Gliner |
| 7,228,167 B2 | 6/2007 | Kara et al. |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,254,439 B2 | 8/2007 | Misczynski et al. |
| 7,263,467 B2 | 8/2007 | Sackellares et al. |
| 7,274,298 B2 | 9/2007 | Frank |
| 7,277,758 B2 | 10/2007 | DiLorenzo |
| 7,280,867 B2 | 10/2007 | Frei et al. |
| 7,282,030 B2 | 10/2007 | Frei et al. |
| 7,289,844 B2 | 10/2007 | Misczynski et al. |
| 7,292,890 B2 | 11/2007 | Whitehurst et al. |
| 7,295,881 B2 | 11/2007 | Cohen et al. |
| 7,299,096 B2 | 11/2007 | Balzer et al. |
| 7,302,298 B2 | 11/2007 | Lowry et al. |
| 7,304,580 B2 | 12/2007 | Sullivan et al. |
| 7,305,268 B2 | 12/2007 | Gliner et al. |
| 7,313,440 B2 | 12/2007 | Miesel |
| 7,314,451 B2 | 1/2008 | Halperin et al. |
| 7,321,837 B2 | 1/2008 | Osorio et al. |
| 7,324,850 B2 | 1/2008 | Persen et al. |
| 7,324,851 B1 | 1/2008 | DiLorenzo |
| 7,330,760 B2 | 2/2008 | Heruth et al. |
| 7,346,391 B1 | 3/2008 | Osorio et al. |
| 7,353,063 B2 | 4/2008 | Simms, Jr. |
| 7,353,064 B2 | 4/2008 | Gliner et al. |
| 7,373,199 B2 | 5/2008 | Sackellares et al. |
| 7,385,443 B1 | 6/2008 | Denison |
| 7,389,144 B1 | 6/2008 | Osorio et al. |
| 7,389,147 B2 | 6/2008 | Wahlstrand et al. |
| 7,395,113 B2 | 7/2008 | Heruth et al. |
| 7,395,216 B2 | 7/2008 | Rosenfeld et al. |
| 7,401,008 B2 | 7/2008 | Frei et al. |
| 7,403,820 B2 | 7/2008 | DiLorenzo |
| 7,420,472 B2 | 9/2008 | Tran |
| 7,433,732 B1 | 10/2008 | Carney et al. |
| 7,437,196 B2 | 10/2008 | Wyler et al. |
| 7,447,545 B2 | 11/2008 | Heruth et al. |
| 7,454,245 B2 | 11/2008 | Armstrong et al. |
| 7,483,747 B2 | 1/2009 | Gliner et al. |
| 7,488,293 B2 | 2/2009 | Marcovecchio et al. |

(56) References Cited

U.S. PATENT DOCUMENTS

| | | |
|---|---|---|
| 7,488,294 B2 | 2/2009 | Torch |
| 7,491,181 B2 | 2/2009 | Heruth et al. |
| 7,494,464 B2 | 2/2009 | Rzesnitzek et al. |
| 7,502,643 B2 | 3/2009 | Farringdon et al. |
| 7,515,054 B2 | 4/2009 | Torch |
| 7,539,532 B2 | 5/2009 | Tran |
| 7,539,533 B2 | 5/2009 | Tran |
| 7,539,543 B2 | 5/2009 | Schiff et al. |
| 7,558,622 B2 | 7/2009 | Tran |
| 7,565,132 B2 | 7/2009 | Ben Ayed |
| 7,590,453 B2 | 9/2009 | Heruth et al. |
| 7,620,456 B2 | 11/2009 | Gliner et al. |
| 7,629,890 B2 | 12/2009 | Sullivan et al. |
| 7,643,655 B2 | 1/2010 | Liang et al. |
| 7,647,121 B2 | 1/2010 | Wahlstrand et al. |
| 7,658,112 B2 | 2/2010 | Nakamura |
| 7,666,151 B2 | 2/2010 | Sullivan et al. |
| 7,714,757 B2 | 5/2010 | Denison et al. |
| 7,717,848 B2 | 5/2010 | Heruth et al. |
| RE41,376 E | 6/2010 | Torch |
| 7,733,224 B2 | 6/2010 | Tran |
| 7,747,318 B2 | 6/2010 | John et al. |
| 7,761,145 B2 | 7/2010 | Virag et al. |
| 7,769,464 B2 | 8/2010 | Gerber et al. |
| 7,775,993 B2 | 8/2010 | Heruth et al. |
| 7,792,583 B2 | 9/2010 | Miesel et al. |
| 7,801,603 B2 | 9/2010 | Westlund et al. |
| 7,801,618 B2 | 9/2010 | Pless |
| 7,801,743 B2 | 9/2010 | Graves et al. |
| 7,813,802 B2 | 10/2010 | Tcheng et al. |
| 7,822,481 B2 | 10/2010 | Gerber et al. |
| 7,827,011 B2 | 11/2010 | DeVaul et al. |
| 7,831,305 B2 | 11/2010 | Gliner |
| 7,847,628 B2 | 12/2010 | Denison |
| 7,866,212 B2 | 1/2011 | Ariav et al. |
| 7,899,545 B2 | 3/2011 | John |
| 7,935,076 B2 | 5/2011 | Estes et al. |
| RE42,471 E | 6/2011 | Torch |
| 7,957,809 B2 | 6/2011 | Bourget et al. |
| 7,965,833 B2 | 6/2011 | Meir et al. |
| 7,974,671 B2 | 7/2011 | Fujiwara et al. |
| 7,996,076 B2 | 8/2011 | Burns et al. |
| 7,999,857 B2 | 8/2011 | Bunn et al. |
| 8,000,789 B2 | 8/2011 | Denison |
| 8,000,794 B2 | 8/2011 | Lozano |
| 8,021,299 B2 | 9/2011 | Miesel et al. |
| 8,027,730 B2 | 9/2011 | John |
| 8,027,737 B2 | 9/2011 | Kokones et al. |
| 8,075,499 B2 | 12/2011 | Nathan et al. |
| 8,109,891 B2 | 2/2012 | Kramer et al. |
| 2001/0032059 A1 | 10/2001 | Kelly, Jr. et al. |
| 2002/0072782 A1 | 6/2002 | Osorio et al. |
| 2002/0082480 A1 | 6/2002 | Riff et al. |
| 2002/0099417 A1 | 7/2002 | Naritoku et al. |
| 2002/0116030 A1 | 8/2002 | Rezai |
| 2002/0151939 A1 | 10/2002 | Rezai |
| 2002/0188214 A1 | 12/2002 | Misczynski et al. |
| 2003/0040680 A1 | 2/2003 | Hassert et al. |
| 2003/0074032 A1 | 4/2003 | Gliner |
| 2003/0083716 A1 | 5/2003 | Nicolelis et al. |
| 2003/0083726 A1 | 5/2003 | Zeijlemaker et al. |
| 2003/0125786 A1 | 7/2003 | Gliner et al. |
| 2003/0130706 A1 | 7/2003 | Sheffield et al. |
| 2003/0144829 A1 | 7/2003 | Geatz et al. |
| 2003/0181954 A1 | 9/2003 | Rezai |
| 2003/0181958 A1 | 9/2003 | Dobak, III |
| 2003/0195588 A1 | 10/2003 | Fischell et al. |
| 2003/0208212 A1 | 11/2003 | Cigaina |
| 2003/0210147 A1 | 11/2003 | Humbard |
| 2003/0212440 A1 | 11/2003 | Boveja |
| 2003/0236474 A1 | 12/2003 | Singh |
| 2003/0236558 A1 | 12/2003 | Whitehurst et al. |
| 2004/0006278 A1 | 1/2004 | Webb et al. |
| 2004/0030365 A1 | 2/2004 | Rubin |
| 2004/0088024 A1 | 5/2004 | Firlik et al. |
| 2004/0111045 A1 | 6/2004 | Sullivan et al. |
| 2004/0122484 A1 | 6/2004 | Hatlestad et al. |
| 2004/0122485 A1 | 6/2004 | Stahmann et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138647 A1 | 7/2004 | Osorio et al. |
| 2004/0138711 A1 | 7/2004 | Osorio et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0172085 A1 | 9/2004 | Knudson et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0199212 A1 | 10/2004 | Fischell et al. |
| 2004/0225335 A1 | 11/2004 | Whitehurst et al. |
| 2004/0249302 A1 | 12/2004 | Donoghue et al. |
| 2004/0249416 A1 | 12/2004 | Yun et al. |
| 2004/0267152 A1 | 12/2004 | Pineda |
| 2005/0004621 A1 | 1/2005 | Boveja et al. |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0022606 A1 | 2/2005 | Partin et al. |
| 2005/0027284 A1 | 2/2005 | Lozano et al. |
| 2005/0033378 A1 | 2/2005 | Sheffield et al. |
| 2005/0033379 A1 | 2/2005 | Lozano et al. |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0060001 A1 | 3/2005 | Singhal et al. |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075701 A1 | 4/2005 | Shafer |
| 2005/0075702 A1 | 4/2005 | Shafer |
| 2005/0101873 A1 | 5/2005 | Misczynski et al. |
| 2005/0107716 A1 | 5/2005 | Eaton et al. |
| 2005/0119703 A1 | 6/2005 | DiLorenzo |
| 2005/0124901 A1 | 6/2005 | Misczynski et al. |
| 2005/0131467 A1 | 6/2005 | Boveja |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0143786 A1 | 6/2005 | Boveja |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1* | 7/2005 | Boveja et al. .................. 607/45 |
| 2005/0177200 A1 | 8/2005 | George et al. |
| 2005/0182389 A1 | 8/2005 | LaPorte et al. |
| 2005/0187590 A1 | 8/2005 | Boveja et al. |
| 2005/0187796 A1 | 8/2005 | Rosenfeld et al. |
| 2005/0192644 A1 | 9/2005 | Boveja et al. |
| 2005/0197590 A1 | 9/2005 | Osorio et al. |
| 2005/0203366 A1 | 9/2005 | Donoghue et al. |
| 2005/0245971 A1 | 11/2005 | Brockway et al. |
| 2005/0261542 A1 | 11/2005 | Riehl |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0288600 A1 | 12/2005 | Zhang et al. |
| 2005/0288760 A1 | 12/2005 | Machado et al. |
| 2006/0009815 A1 | 1/2006 | Boveja et al. |
| 2006/0018833 A1 | 1/2006 | Murphy et al. |
| 2006/0074450 A1 | 4/2006 | Boveja et al. |
| 2006/0079936 A1 | 4/2006 | Boveja et al. |

(56) References Cited

U.S. PATENT DOCUMENTS

| | | |
|---|---|---|
| 2006/0094971 A1 | 5/2006 | Drew |
| 2006/0094972 A1 | 5/2006 | Drew |
| 2006/0095081 A1 | 5/2006 | Zhou et al. |
| 2006/0106430 A1 | 5/2006 | Fowler et al. |
| 2006/0111644 A1 | 5/2006 | Guttag et al. |
| 2006/0122525 A1 | 6/2006 | Shusterman |
| 2006/0122864 A1 | 6/2006 | Gottesman et al. |
| 2006/0135877 A1* | 6/2006 | Giftakis et al. ............... 600/513 |
| 2006/0135881 A1 | 6/2006 | Giftakis et al. |
| 2006/0149139 A1 | 7/2006 | Bonmassar et al. |
| 2006/0155495 A1 | 7/2006 | Osorio et al. |
| 2006/0161459 A9 | 7/2006 | Rosenfeld et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195163 A1 | 8/2006 | KenKnight et al. |
| 2006/0200206 A1 | 9/2006 | Firlik et al. |
| 2006/0212091 A1 | 9/2006 | Lozano et al. |
| 2006/0212097 A1 | 9/2006 | Varadan et al. |
| 2006/0224067 A1 | 10/2006 | Giftakis et al. |
| 2006/0224191 A1 | 10/2006 | Dilorenzo |
| 2006/0241697 A1 | 10/2006 | Libbus et al. |
| 2006/0241725 A1 | 10/2006 | Libbus et al. |
| 2006/0293720 A1 | 12/2006 | DiLorenzo |
| 2007/0027486 A1 | 2/2007 | Armstrong |
| 2007/0027497 A1 | 2/2007 | Parnis |
| 2007/0027498 A1 | 2/2007 | Maschino et al. |
| 2007/0027500 A1 | 2/2007 | Maschino et al. |
| 2007/0032734 A1 | 2/2007 | Najafi et al. |
| 2007/0032834 A1 | 2/2007 | Gliner et al. |
| 2007/0043392 A1 | 2/2007 | Gliner et al. |
| 2007/0055320 A1 | 3/2007 | Weinand |
| 2007/0073150 A1 | 3/2007 | Gopalsami et al. |
| 2007/0073355 A1 | 3/2007 | Dilorenzo |
| 2007/0088403 A1 | 4/2007 | Wyler et al. |
| 2007/0088404 A1 | 4/2007 | Wyler et al. |
| 2007/0100278 A1 | 5/2007 | Frei et al. |
| 2007/0100392 A1 | 5/2007 | Maschino et al. |
| 2007/0142862 A1 | 6/2007 | Dilorenzo |
| 2007/0142873 A1 | 6/2007 | Esteller et al. |
| 2007/0149952 A1 | 6/2007 | Bland et al. |
| 2007/0150024 A1 | 6/2007 | Leyde et al. |
| 2007/0150025 A1 | 6/2007 | Dilorenzo et al. |
| 2007/0156450 A1 | 7/2007 | Roehm et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0173902 A1 | 7/2007 | Maschino et al. |
| 2007/0179534 A1 | 8/2007 | Firlik et al. |
| 2007/0179557 A1 | 8/2007 | Maschino et al. |
| 2007/0179558 A1 | 8/2007 | Gliner et al. |
| 2007/0208212 A1 | 9/2007 | DiLorenzo |
| 2007/0213785 A1 | 9/2007 | Osorio et al. |
| 2007/0233192 A1 | 10/2007 | Craig |
| 2007/0239210 A1 | 10/2007 | Libbus et al. |
| 2007/0242661 A1 | 10/2007 | Tran |
| 2007/0244407 A1 | 10/2007 | Osorio |
| 2007/0249953 A1 | 10/2007 | Frei et al. |
| 2007/0249954 A1 | 10/2007 | Virag et al. |
| 2007/0255147 A1 | 11/2007 | Drew et al. |
| 2007/0255155 A1 | 11/2007 | Drew et al. |
| 2007/0260147 A1 | 11/2007 | Giftakis et al. |
| 2007/0260289 A1 | 11/2007 | Giftakis et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2007/0287931 A1 | 12/2007 | Dilorenzo |
| 2008/0004904 A1 | 1/2008 | Tran |
| 2008/0021341 A1 | 1/2008 | Harris et al. |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0033503 A1 | 2/2008 | Fowler et al. |
| 2008/0033508 A1 | 2/2008 | Frei et al. |
| 2008/0046035 A1 | 2/2008 | Fowler et al. |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0081958 A1 | 4/2008 | Denison et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146890 A1 | 6/2008 | LeBoeuf et al. |
| 2008/0146958 A1* | 6/2008 | Guillory et al. ............... 600/544 |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0208013 A1 | 8/2008 | Zhang et al. |
| 2008/0208074 A1* | 8/2008 | Snyder et al. ............... 600/545 |
| 2008/0208284 A1 | 8/2008 | Rezai et al. |
| 2008/0208781 A1 | 8/2008 | Snyder |
| 2008/0234598 A1* | 9/2008 | Snyder et al. ............... 600/545 |
| 2008/0255582 A1 | 10/2008 | Harris |
| 2008/0258907 A1 | 10/2008 | Kalpaxis |
| 2008/0269579 A1 | 10/2008 | Schiebler |
| 2008/0275327 A1 | 11/2008 | Faarbaek et al. |
| 2008/0275328 A1 | 11/2008 | Jones |
| 2008/0275349 A1 | 11/2008 | Halperin et al. |
| 2008/0281376 A1 | 11/2008 | Gerber et al. |
| 2008/0281381 A1 | 11/2008 | Gerber et al. |
| 2008/0281550 A1 | 11/2008 | Hogle et al. |
| 2008/0319281 A1 | 12/2008 | Aarts |
| 2009/0030345 A1 | 1/2009 | Bonnet et al. |
| 2009/0040052 A1 | 2/2009 | Cameron et al. |
| 2009/0054737 A1 | 2/2009 | Magar et al. |
| 2009/0054742 A1 | 2/2009 | Kaminska et al. |
| 2009/0054795 A1 | 2/2009 | Misczynski et al. |
| 2009/0060287 A1 | 3/2009 | Hyde et al. |
| 2009/0076350 A1 | 3/2009 | Bly et al. |
| 2009/0099624 A1 | 4/2009 | Kokones et al. |
| 2009/0099627 A1 | 4/2009 | Molnar et al. |
| 2009/0105785 A1 | 4/2009 | Wei et al. |
| 2009/0124923 A1* | 5/2009 | Sackellares et al. ......... 600/544 |
| 2009/0137921 A1 | 5/2009 | Kramer et al. |
| 2009/0227882 A1 | 9/2009 | Foo |
| 2009/0227888 A1 | 9/2009 | Salmi et al. |
| 2009/0291150 A1* | 11/2009 | Welsh ..................... A61K 31/00 424/700 |
| 2009/0322540 A1 | 12/2009 | Richardson et al. |
| 2010/0010382 A1 | 1/2010 | Panken |
| 2010/0010392 A1 | 1/2010 | Skelton et al. |
| 2010/0010583 A1 | 1/2010 | Panken et al. |
| 2010/0023348 A1 | 1/2010 | Hardee et al. |
| 2010/0056878 A1 | 3/2010 | Partin et al. |
| 2010/0106217 A1 | 4/2010 | Colborn |
| 2010/0109875 A1 | 5/2010 | Ayon et al. |
| 2010/0121214 A1* | 5/2010 | Giftakis et al. ............... 600/544 |
| 2010/0168603 A1* | 7/2010 | Himes et al. ................. 600/544 |
| 2010/0217533 A1 | 8/2010 | Nadkarni et al. |
| 2010/0223020 A1 | 9/2010 | Goetz |
| 2010/0228103 A1 | 9/2010 | Schecter |
| 2010/0228314 A1 | 9/2010 | Goetz |
| 2010/0268056 A1 | 10/2010 | Picard et al. |
| 2010/0274303 A1 | 10/2010 | Bukhman |
| 2010/0280336 A1 | 11/2010 | Giftakis et al. |
| 2010/0280578 A1 | 11/2010 | Skelton et al. |
| 2010/0280579 A1 | 11/2010 | Denison et al. |
| 2010/0286567 A1 | 11/2010 | Wolfe et al. |
| 2010/0298661 A1 | 11/2010 | McCombie et al. |
| 2010/0298742 A1 | 11/2010 | Perlman et al. |
| 2010/0305665 A1 | 12/2010 | Miesel et al. |
| 2010/0312188 A1 | 12/2010 | Robertson et al. |
| 2011/0029044 A1 | 2/2011 | Hyde et al. |

(56) References Cited

U.S. PATENT DOCUMENTS

| | | |
|---|---|---|
| 2011/0040204 A1 | 2/2011 | Ivorra et al. |
| 2011/0040546 A1 | 2/2011 | Gerber et al. |
| 2011/0060252 A1 | 3/2011 | Simonsen et al. |
| 2011/0066062 A1 | 3/2011 | Benet et al. |
| 2011/0066081 A1 | 3/2011 | Goto |
| 2011/0137372 A1 | 6/2011 | Makous et al. |
| 2011/0172545 A1 | 7/2011 | Grudic et al. |
| 2011/0230730 A1 | 9/2011 | Quigg et al. |
| 2011/0245629 A1 | 10/2011 | Giftakis et al. |
| 2011/0251468 A1 | 10/2011 | Osorio |
| 2011/0251469 A1 | 10/2011 | Varadan |
| 2011/0270117 A1 | 11/2011 | Warwick et al. |
| 2011/0270134 A1 | 11/2011 | Skelton |
| 2011/0295127 A1 | 12/2011 | Sandler et al. |
| 2011/0306845 A1 | 12/2011 | Osorio |
| 2011/0306846 A1 | 12/2011 | Osorio |
| 2011/0313484 A1 | 12/2011 | Hincapie Ordonez et al. |
| 2012/0226108 A1* | 9/2012 | Osorio ............... A61N 1/37258 600/301 |
| 2012/0271372 A1* | 10/2012 | Osorio ........................... 607/17 |
| 2012/0296175 A1* | 11/2012 | Poh et al. ..................... 600/301 |
| 2013/0116514 A1* | 5/2013 | Kroner et al. ................ 600/301 |

FOREIGN PATENT DOCUMENTS

| | | |
|---|---|---|
| EP | 1486232 A2 | 12/2004 |
| GB | 2026870 A | 2/1980 |
| GB | 2079610 A | 1/1982 |
| WO | 9302744 A1 | 2/1993 |
| WO | 0064336 A1 | 11/2000 |
| WO | 2004036377 A2 | 4/2004 |
| WO | 2005007120 A2 | 1/2005 |
| WO | 2005053788 A1 | 6/2005 |
| WO | 2005067599 A2 | 7/2005 |
| WO | 2006050144 A1 | 5/2006 |
| WO | 2006122148 A2 | 11/2006 |
| WO | 2006134359 A1 | 12/2006 |
| WO | 2007066343 A2 | 6/2007 |
| WO | 2007072425 A2 | 6/2007 |
| WO | 2007124126 A2 | 11/2007 |
| WO | 2007124190 A2 | 11/2007 |
| WO | 2007124192 A1 | 11/2007 |
| WO | 2007142523 A1 | 12/2007 |
| WO | 2008045597 A1 | 4/2008 |
| WO | 2008054580 A2 | 5/2008 |
| WO | 2011126931 A1 | 10/2011 |

OTHER PUBLICATIONS

Bachman, D. et al., "Effects of Vagal Volleys and Serotonin on Units of Cingulate Cortex in Monkeys", Brain Research, vol. 130, 1977, pp. 253-269.

Baevskii, R., "Analysis of Heart Rate Variability in Space Medicine", Human Physiology, vol. 28, No. 2, 2002, pp. 202-213.

Baevsky, R., "Autonomic cardiovascular and respiratory control during prolonged spaceflights aboard the International Space Station", Journal of Applied Physiological, vol. 103, 2007, pp. 156-161.

Boon, P. et al., "Programmed and Magnet-Induced Vagus Nerve Stimulation for Refractory Epilepsy", Journal of Clinical Neurophysiology, vol. 18, No. 5, 2001, p. 402-407.

Boon, P. et al., "Vagus Nerve Stimulation for Epilepsy, Clinical Efficacy of Programmed and Magnet Stimulation", Acta Neurochirurgica Supplement, vol. 79, 2002, pp. 93-98.

Borovikova, L. et al., "Vagus Nerve Stimulation Attenuates the Systemic Inflammatory Response to Endotoxin", Letters to Nature, vol. 405, May 2000, pp. 458-462.

Brack, K. et al., "Interaction Between Direct Sympathetic and Vagus Nerve Stimulation on Heart Rate in the Isolated Rabbit Heart", Experimental Physiology, vol. 89, No. 1, 2004, pp. 128-139.

Chakravarthy, N. et al., "Controlling Synchronization in a Neuron-Level Population Model", International Journal of Neural Systems, vol. 17, No. 2, 2007, pp. 123-138.

Clark, K. et al., "Posttraining Electrical Stimulation of Vagal Afferents with Concomitant Vagal Efferent Inactivation Enhances Memory Storage Processes in the Rat", Neurobiology of Learning and Memory, vol. 70, Article No. NL983863, 1998, pp. 364-373.

Digenarro, G. et al., "Ictal Heart rate Increase Precedes EEG Discharge in Drug-Resistant Mesial Temporal Lobe Seizures", Clinical Neurophysiology, vol. 115, No. 5, May 2004, pp. 1169-1177.

Van Elmpt, W. et al., "A Model of Heart Rate Changes to Detect Seizures in Severe Epilepsy", Seizure, vol. 15, 2006, pp. 366-375.

Frei, M. et al., "Left Vagus Nerve Stimulation with the Neurocybernetic Prosthesis has Complex Effects on Heart Rate and on its Variability in Humans", Epilepsia, vol. 42, No. 8, 2001, pp. 1007-1016.

George, M. et al., "Vagus Nerve Stimulation: A New Tool for Brain Research and Therapy", Society of Biological Psychiatry, vol. 47, 2000, pp. 287-295.

Hallowitz, R. et al., "Effects of Vagal Volleys on Units of Intralaminar and Juxtalaminar Thalamic Nuclei in Monkeys", Brain Research, vol. 130, No. 2, Jul. 1977, pp. 271-286.

Henry, T., "Therapeutic Mechanisms of Vague Name Stimulation", Neurology, vol. 59 (Supp. 4), Sep. 2002, pp. S3-S14.

Iasemidis, L. et al., "Dynamical Resetting of the Human Brain at Epileptic: Application of Nonlinear Dynamics and Global Optimization Techniques", IEEE Transactions on Biomedical Engineering, vol. 51, No. 3, Mar. 2004, pp. 493-508.

Iasemidis, L. et al., "Spatiotemporal Transition to Epileptic Seizures: A Nonlinear Dynamical Analysis of Scalp and Intracranial EEG Recordings", Spatiotemporal Models in Biological and Artificial Systems, IOS Press, 1997, pp. 81-88.

Iasemidis, L., "Epileptic Seizure Prediction and Control", IEEE Transactions on Biomedical Engineering, vol. 50, No. 5, May 2003, pp. 549-558.

Kautzner, J. et al., "Utility of Short-Term Heart Rate Variability for Prediction of Sudden Cardiac Death After Acute Myocardial Infarction", Acta Univ Palacki Olomuc Fac Med., vol. 141, 1998, pp. 69-73.

Koenig, S. et al., "Vagus Nerve Stimulation Improves Severely Impaired Heart Rate Variability in a Patient with Lennox-Gastaut-Syndrome", Seizure, vol. 17, Issue 5, Jul. 2008, pp. 469-472.

Koo, B., "EEG Changes with Vagus Nerve Stimulation", Journal of Clinical Neurophysiology, vol. 18, No. 5, Sep. 2001, pp. 434-441.

Krittayaphong, M. et al., "Heart Rate Variability in Patients with Coronary Artery Disease: Differences in Patients with Higher and Lower Depression Scores", Psychosomatic Medicine, vol. 59, 1997, pp. 231-235.

Leutmezer, F. et al., "Electrocardiographic Changes at the Onset of Epileptic Seizures", Epilepsia, vol. 44, No. 3, 2003, pp. 348-354.

Lewis, M. et al., "Vagus Nerve Stimulation Decreases Left Ventricular Contractility in Vivo in the Human and Pig Heart", The Journal of Physiology, vol. 534, No. 2, 2001, pp. 547-552.

Li, M. et al., "Vagal Nerve Stimulation Markedly Improves Long-Term Survival After Chronic Heart Failure in Rats", Circulation, Jan. 2004, vol. 109, No. 1, pp. 120-124.

Licht, C., "Association Between Major Depressive Disorder and Heart Rate Variability in the Netherlands Study of Depression and Anxiety (NESDA)", Arch. Gen. Psychiatry, vol. 65, No. 12, Dec. 2008, pp. 1358-1367.

Lockard, J. et al., "Feasibility and safety of vagal stimulation in monkey model", Epilepsia, vol. 31 (Supp. 2), 1990, pp. S20-S26.

Long, T. et al., "Effectiveness of Heart Rate Seizure Detection Compared to EEG in an Epilepsy Monitoring Unit (EMU)", Abstract of AES Proceedings, Epilepsia, vol. 40, Supplement 7, 1999, p. 174.

McClintock, P., "Can Noise Actually Boost Brain Power", Physics World, Jul. 2002, vol. 15, pp. 20-21.

Mori, T. et al., "Noise-Induced Entrainment and Stochastic Resonance in Human Brain Waves", Physical Review Letters, vol. 88, No. 21, 2002, pp. 218101-1-2180101-4.

Mormann, F. et al., "Seizure Prediction: The Long and Winding Road", Brain, vol. 130, 2007, pp. 314-333.

Nouri, M., "Epilepsy and the Autonomic Nervous System", emedicine, Updated May 5, 2006, http://www.emedicine.com/neuro/toplo658.htm, pp. 1-14.

(56) References Cited

OTHER PUBLICATIONS

O'Donovan, C. et al., "Computerized Seizure Detection Based on Heart Rate Changes", Abstract of AES Proceedings, Epilepsia, vol. 36, Supplement 4, 1995, p. 7.
O'Regan, M. et al., "Abnormalities in Cardiac and Respiratory Function Observed During Seizures in Childhood", Developmental Medicine & Child Neurology, vol. 47, 2005, pp. 4-9.
Osorio, I. et al., "An Introduction to Contingent (Closed-Loop) Brain Electrical Stimulation for Seizure Blockage, to Ultra-Short-Term Clinical Trials, and to Multidimensional Statistical Analysis of Therapeutic Efficacy", Journal of Clinical Neurophysiology, vol. 18, No. 6, 2001, pp. 533-544.
Osorio, I. et al., "Automated Seizure Abatement in Humans Using Electrical Stimulation", Annals of Neurology, vol. 57, No. 2, 2005, pp. 258-268.
Osorio, I. et al., "Toward a Quantitative Multivariate Analysis of the Efficacy of Antiseizure Therapies", Epilepsy & Behavior, vol. 18, No. 4, Aug. 2010, Academic Press, San Diego, CA, pp. 335-343.
Pathwardhan, R. et al., "Control of Refractory Status Epilepticus Precipitated by Anticonvulsant Withdrawal Using Vagal Nerve Stimulation: A Case Report", Surgical Neurology, Issue 64, Aug. 2005, pp. 170-173.
PCT Search Report and Written Opinion for International application No. PCT/US2011/054287, dated Mar. 12, 2012, 18 pages.
PCT Search Report and Written Opinion for International Application No. PCT/US2012/027639, dated Oct. 4, 2012, 22 pages.
Poddubnaya, E., "Complex Estimation of Adaption Abilities of the Organism in Children Using the Indices of Responsiveness of the Cardiovascular System and Characteristics of EEG", Neurophysiology, vol. 38, No. 1, 2006, pp. 63-74.
Robinson, S. et al., "Heart Rate Variability Changes as Predictor of Response to Vagal Nerve Stimulation Therapy for Epilepsy", Abstract of AES Proceedings, Epilepsia, vol. 40, Supplement 7, 1999, p. 147.
Rugg-Gunn, F. et al., "Cardiac Arrhythmias in Focal Epilepsy: a Prospective Long-Term Study", Lancet, vol. 364, Dec. 2004, pp. 2212-2219.
Sajadieh, A. et al., "Increased Heart Rate and Reduced Heart-rate Variability and Associated with Subclinical Inflammation in Middle-Aged and Elderly Subjects with No Apparent Heart Disease", European Heart Journal, vol. 25, 2004, pp. 363-370.
Schernthaner, C. et al., "Autonomic Epilepsy—The Influence of Epileptic Discharges on Heart Rate and Rhythm", The Middle European Journal of Medicine, vol. 111, No. 10, 1999, pp. 392-401.
Sunderam, S. et al., "Vagal and Sciatic Nerve Stimulation Have Complex, Time-Dependent Effects on Chemically-Induced Seizures: A Controlled Study", Brain Research, vol. 918, 2001, pp. 60-66.
Terry, R. et al., "The Implantable Neurocybernetic Prosthesis System", Pacing and Clinical Electrophysiology, vol. 14, No. 1, Jan. 1991, pp. 86-93.
Tubbs, R. et al., "Left-Sided Vagus Nerve Stimulation Decreases Intracranial Pressure Without Resultant Bradycardia in the Pig: A Potential Therapeutic Modality for Humans", Child's Nervous System, vol. 20, No. 5, May 2004, pp. 309-312.
Umetani, M. et al., "Twenty-Four Hour Time Domain Heart Rate Variability and Heart Rate: Relations to Age and Gender Over Nine Decades", JACC, vol. 31, No. 3, Mar. 1998, pp. 593-601.
Vonck, K. et al., "The Mechanism of Action of Vagus Nerve Stimulation for Refractory Epilepsy—The Current Status", Journal of Neurophysiology, vol. 18, No. 5, 2001, pp. 394-401.
Weil, S. et al., "Heart Rate Increase in Otherwise Subclinical Seizures is Different in Temporal Versus Extratemporal Seizure Onset: Support for Temporal Lobe Automatic Influence", Epileptic Disord., vol. 7, No. 3, Sep. 2005, pp. 199-204.
Woodbury, J. et al., "Vagal stimulation reduces the severity of maximal electroshock seizures in intact rats: use of a cuff electrode for stimulating and recording", Pacing and Clinical Electrophysiology, vol. 14, Jan. 1991, pp. 94-107.
Zabara, J. et al., "Neuroinhibition in the regulation of emesis", Space Life Sciences, vol. 3, Issue 3, Jun. 1972, pp. 282-292.
Zabara, J., "Inhibition of Experimental Seizures in Canines by Repetitive Vagal Stimulation", Epilepsia, vol. 33, No. 6, 1992, pp. 1005-1012.
Zabara, J., "Neural Control of Circulation I", The Physiologist, vol. 28, No. 4, Aug. 1985, pp. 273-277.
Zabara, J., "Neuroinhibition of Xylaine Induced Emesis", Pharmacology & Toxicology, vol. 63, Aug. 1988, pp. 70-74.
Zijlmans, M. et al., "Heart Rate Changes and ECG Abnormalities During Epileptic Seizures: Prevalence and Definition of an Objective Clinical Sign", Epilepsia, vol. 43, No. 8, 2002, pp. 847-854.
International Search Report and Written Opinion for PCT Patent Application No. PCT/US2013/037703, dated Aug. 23 2013, 12 pages.
Lhatoo, Samden, D. et al, "An Electroclinical Case-Control Study of Sudden Unexpected Death in Epilepsy," Annals of Neurology, 68(6): 787-796, Dec. 29, 2010.
Seyal et al., "Postictal Generalized EEG Suppression Is Linked to Seizure-Associated Respiratory Dysfunction But Not Postictal Apnea," Epilepsia, 53(5): 825-831, Mar. 20, 2012.
So, et al., "Postical Central Apnea As a Cause of SUDEP: Evidence From Near-SUDEP Incident," Epilepsia, 41(11): 1494-1497, Nov. 1, 2000.

\* cited by examiner

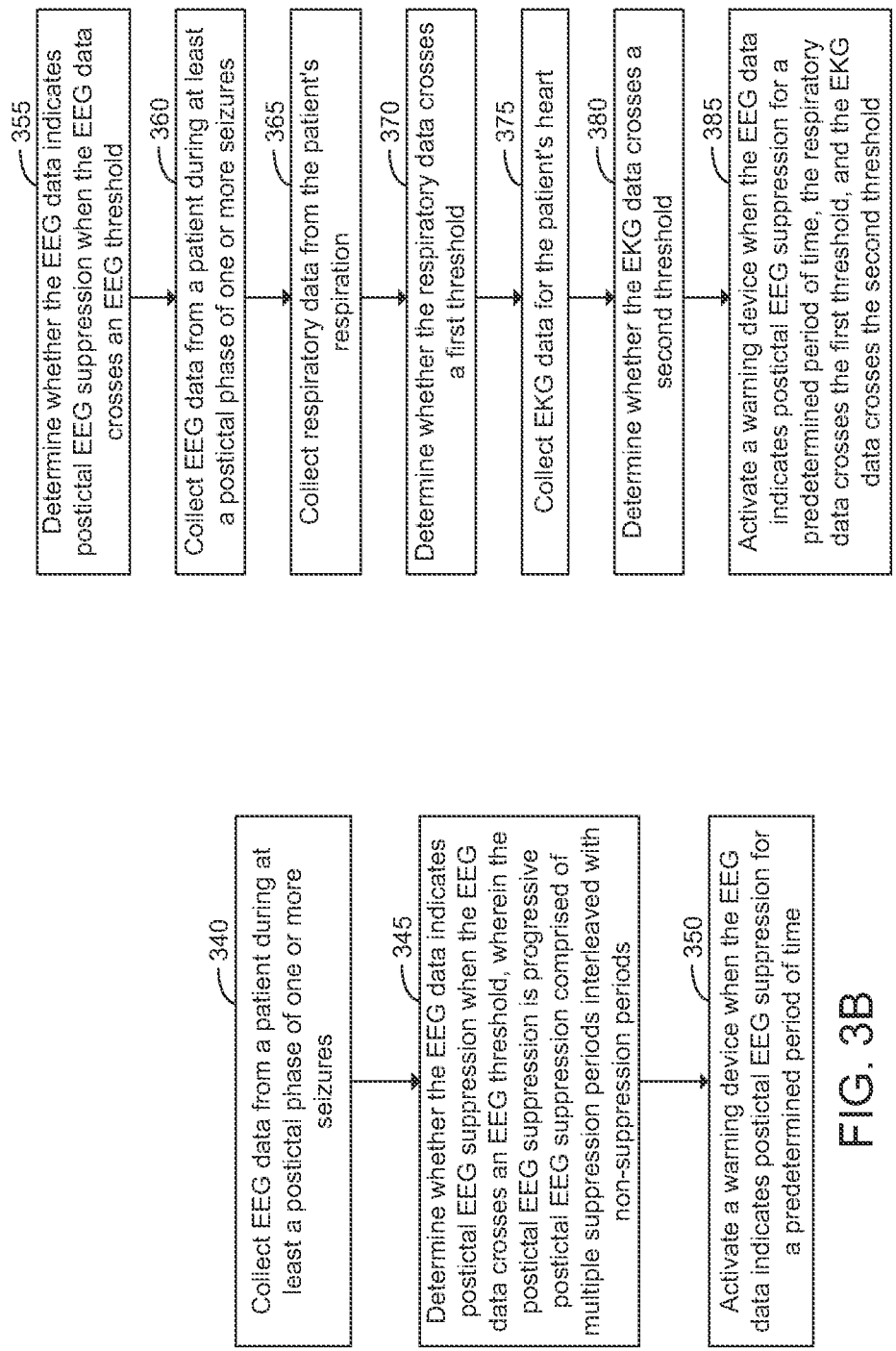

METHODS, SYSTEMS AND APPARATUSES FOR DETECTING INCREASED RISK OF SUDDEN DEATH

FIELD OF THE DISCLOSURE

The present disclosure relates generally to systems, methods, and apparatuses for detecting medical conditions. More particularly, the disclosure relates to systems, methods and apparatuses for detecting medical conditions relating to seizures, especially conditions that may place a patient experiencing a seizure at greater risk of sudden death.

BACKGROUND OF THE DISCLOSURE

The embodiments described herein relate generally to the field of medical detection systems for patients experiencing seizures. "A seizure is an abnormal, unregulated electrical charge that occurs within the brain's cortical gray matter and transiently interrupts normal brain function." *The Merck Manual of Diagnosis and Therapy*, 1822 (M. Beers Editor in Chief, 18th ed. 2006) ("Merck Manual"). Epilepsy is a chronic disease characterized by such seizures, but not caused by an event such as a stroke, drug use or physical injury. Seizures may vary in frequency and scope and may range from involving no impairment of consciousness at all to complete loss of consciousness. Typically, a seizure resolves within a few minutes and extraordinary medical intervention, other than that needed for the comfort of the patient and to promote unobstructed breathing, is not needed. (See, generally, *Merck Manual* at 1822-1827, incorporated herein by reference.)

But in some cases, a seizure may lead to death. Asphyxia is an impairment or absence of the oxygen and carbon dioxide exchange in the body, which can occur, for example, during suffocation. Asphyxia is considered to be the leading cause of Sudden Unexplained Death in Epileptic Patients ("SUDEP") and may indeed trigger SUDEP. But the mechanism and relationship of SUDEP with cardiorespiratory and cerebral function has been poorly understood. SUDEP does not occur during or, generally, immediately after an initial phase of a seizure but as the patient appears to be recovering from the seizure. In addition, SUDEP may occur at night, while the patient is sleeping. Such sudden unexplained death is not necessarily limited to seizure patients and may be underreported in the general population. But seizure patients, including those with epilepsy, seem to be at a higher risk for sudden unexplained death than the general population.

In a typical seizure condition, there are three phases: ictal, post ictal (or "postictal"), and interictal. The ictal phase is the initial portion of the seizure, where a patient may display symptoms, if any, such as convulsions. Generally speaking, the interictal phase is the period between seizures when the patient has substantially recovered.

A postictal phase takes place immediately after the ictal phase of the seizure, where symptoms have subsided, but the patient has not yet returned to normal. During the postictal period, the patient may be relaxed or lying down and may appear to be sleeping. In the postictal period, the patient's heart rate may typically take a few minutes to return to the patient's non-seizure baseline. The same is true of the patient's electrocardiogram ("EKG" or "ECG") measurements, if the patient should happen to be undergoing EKG testing at the time of the seizure. EKG measurements provide a record of the heart's integrated action over a period of time. Cardiac and respiratory readings for the patient soon appear to be normal as the patient progresses in the postictal period. Such measurements and readings, along with visual observation, would support a view that a patient is coming out of the seizure in a normal fashion and is not at risk for SUDEP. One might thus conclude that no medical intervention is necessary. But in some cases, such measurements, readings and observations would be deceptive and the patient is at risk of SUDEP.

If a condition in a patient that leads to an increased risk of SUDEP can be detected, timely measures may be taken that would reduce that risk and possibly save the patient.

Accordingly, a need is present for methods, systems and apparatuses to detect one or more conditions in a patient that may lead to SUDEP and/or overcome issues discussed above.

SUMMARY

The embodiments of the disclosure described herein include a system for identification of an increased risk of a severe neurological event. The system may include an electroencephalogram ("EEG") monitoring unit configured to collect EEG data from the patient during at least a postictal phase of one or more seizures and a processing unit configured to receive the EEG data from the EEG monitoring unit. The processing unit is configured to detect postictal EEG suppression from the EEG data and to identify the increased risk of the severe neurological event based on the detected postictal EEG suppression.

The embodiments of the disclosure described herein also include a system for identification of an increased risk of a severe neurological event. The system includes an electroencephalogram ("EEG") monitoring unit, a processing unit, a respiratory monitoring unit and an electrocardiogram ("EKG") monitoring unit. The electroencephalogram ("EEG") monitoring unit is configured to collect EEG data from the patient's brain during at least a postictal phase of one or more seizures. The processing unit is configured to receive the EEG data from the EEG monitoring unit and to detect postictal EEG suppression from the EEG data when the EEG data crosses an EEG threshold for at least a predetermined time period. The respiratory monitoring unit is configured to collect respiratory data from the patient's respiration during at least the postictal phase of the one or more seizures in response to detection of the postictal EEG suppression. The processing unit receives the respiratory data from the respiratory monitoring unit and determines whether the respiratory data crosses a respiratory threshold. The electrocardiogram ("EKG") monitoring unit is configured to collect EKG data for the patient's heart. The processing unit is configured to receive the EKG data from the EKG monitoring unit and to determine whether the EKG data crosses an EKG threshold. The processing unit is further configured to determine whether the EKG data crosses the EKG threshold in response to a determination that the respiration data crosses the respiration threshold. The processor may identify the increased risk of the severe neurological event based on the detected postictal EEG suppression, the determination that the respiration data crosses the respiration threshold, and the determination that the EKG data crosses the EKG threshold.

The embodiments of the disclosure described herein also include a method for detecting a condition in a patient that poses an increased risk of sudden unexplained death in epilepsy (SUDEP), including collecting encephalogram ("EEG") data from a patient during at least a postictal phase of one or more seizures, and determining whether the EEG data indicates postictal EEG suppression when the EEG data crosses an EEG threshold.

Other aspects and advantages of the embodiments described herein will become apparent from the following description and the accompanying drawings, illustrating the principles of the embodiments by way of example only.

BRIEF DESCRIPTION OF THE DRAWINGS

Features and advantages of the present disclosure will become apparent from the appended claims, the following detailed description of one or more example embodiments, and the corresponding figures.

FIGS. 3A-C are depictions of flowcharts for a process and methods in accordance with one or more embodiments of the present disclosure.

Figure 1:
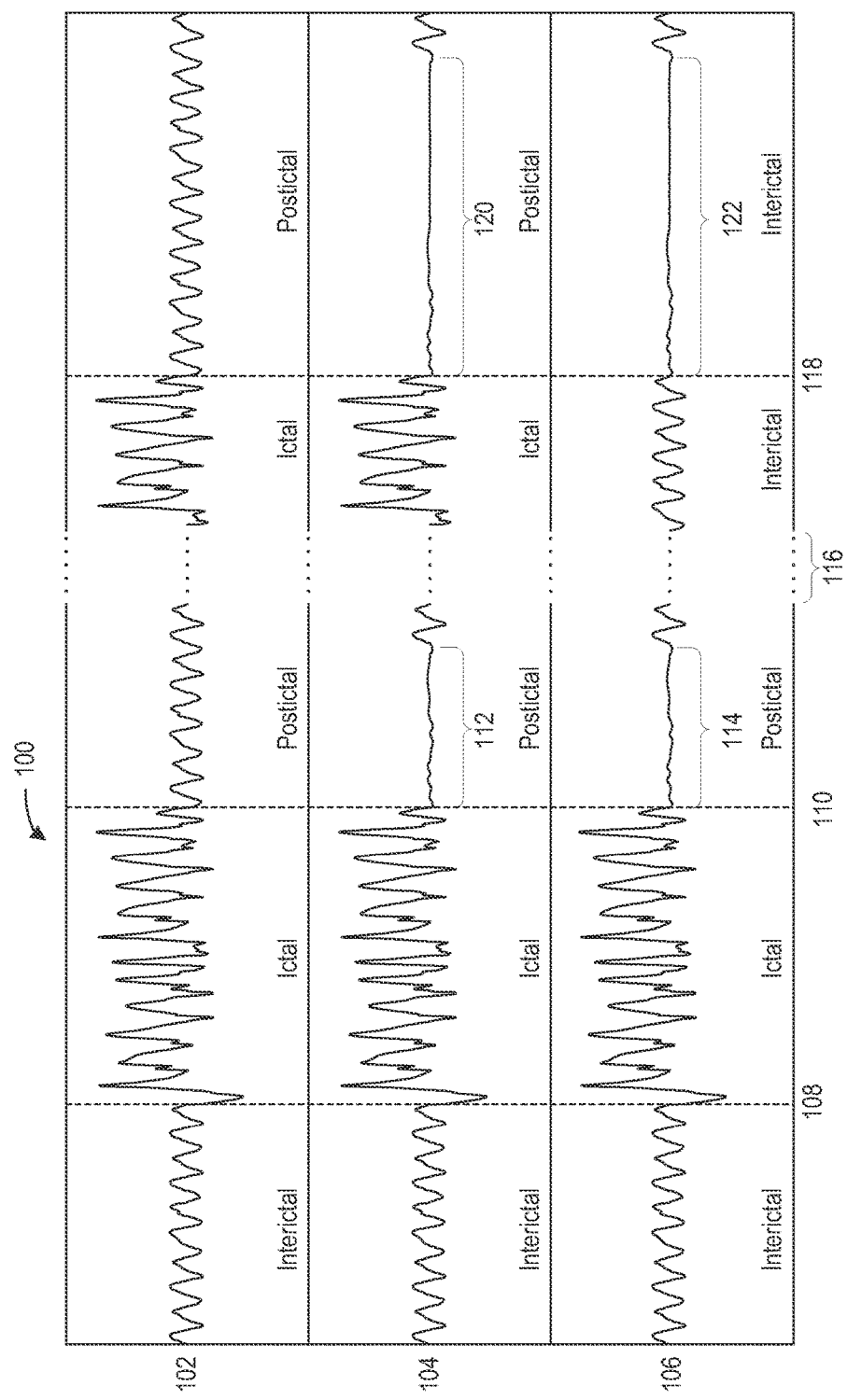
FIG. 1 is a graph depicting EEG measurements where a first patient is recovering normally and a second and third patient start exhibiting EEG suppression indicative of an increased risk of SUDEP.

While the disclosure is subject to various modifications and alternative forms, specific embodiments thereof are shown by way of example in the drawings and the accompanying detailed description. It should be understood, however, that the drawings and detailed description are not intended to limit the invention to the particular embodiments. This disclosure is instead intended to cover all modifications, equivalents, and alternatives falling within the scope of the present invention as defined by the appended claims.

DETAILED DESCRIPTION

The drawing figures are not necessarily to scale and certain features may be shown exaggerated in scale or in somewhat generalized or schematic form in the interest of clarity and conciseness. In the description which follows, like parts may be marked throughout the specification and drawing with the same reference numerals. The foregoing description of the figures is provided for a more complete understanding of the drawings. It should be understood, however, that the embodiments are not limited to the precise arrangements and configurations shown. Although the design and use of various embodiments are discussed in detail below, it should be appreciated that the present disclosure provides many inventive concepts that may be embodied in a wide variety of contexts. The specific aspects and embodiments discussed herein are merely illustrative of ways to make and use the disclosure, and do not limit the scope of the disclosure. It would be impossible or impractical to include all of the possible embodiments and contexts in this disclosure. Upon reading this disclosure, many alternative embodiments of the present disclosure will be apparent to persons of ordinary skill in the art.

TABLE 1

| Identification | Mean EEG Seizure Duration | Clinical Seizure Duration | EKG Seizure Duration | Postictal Breathing (Y/N) |
| --- | --- | --- | --- | --- |
| 1 (10 sz) | 2.24 min. | 1.96 min | 4.85 min | Y |
| 2 (11 sz) | 1.89 min. | 1.69 min. | 4.18 min. | Y |
| 3 (7 sz) | 1.77 min | 1.71 min. | 4.02 min. | Y |

Table 1 compares seizure duration as determined by different types of measurements. These measurements include EKG measurements, clinical measurements which are based on visual observations of the patient, and electroencephalogram ("EEG") readings. In contrast to EKG devices which measure heart activity, EEG devices measure brain activity, often in several parts of the brain at once. Note that the mean EEG seizure duration differs from both the clinical and EKG measurements in these examples being longer than clinical duration and shorter than EKG seizure duration. This is because the brain behavior of patients having seizures can be quite different from the patient's cardiac and respiratory behavior. The EEG indications of seizure are considered the most accurate and EEG variation will typically begin a few seconds before a patient begins experiencing physical symptoms, i.e. when the clinical duration begins. The EKG measurements in the EKG seizure duration column indicate that the heart generally takes longer to return to baseline than either the EEG measurements or the clinical observations would indicate. The far right hand column of Table 1 indicates that postictal breathing was present.

FIG. 1 is a graph 100 depicting EEG measurements where a first patient is recovering normally and a second and third patient start exhibiting EEG suppression indicative of an increased risk of SUDEP. The graph 100 includes three EEG waveforms. A first EEG waveform 102 shows EEG data of a patient having seizures and recovering normally. A second EEG waveform 104 shows EEG data of a patient having multiple seizures and experiencing at least one EEG suppression during the postical phase of each seizure. A third EEG waveform 106 shows EEG data of a patient having seizures and experiencing multiple EEG suppressions during the postical and interictal phase after a single seizure. Waveforms 102, 104, and 106 each start with a normal EEG signal during an interictal phase. The interictal phase ends at time 108 and the itcal phase begins with the onset of a seizure. The seizure shown in waveforms 102, 104, and 106 ends at time 110 and the patients enter a postictal phase. The EEG waveform 102 shows a normal recovery during the postictal phase. The EEG waveform 104 shows a period of EEG suppression 112 and EEG waveform 106 also shows a period of EEG suppression 114. During EEG suppression periods 112 and 114, the amplitudes of the corresponding EEG waveforms are greatly suppressed and appear flat. These EEG suppression periods indicate a significant reduction in brain activity of the patient. The EEG waveforms 104 and 106 show that the patients EEG signal returns to normal and each of the EEG waveforms 102, 104, and 106 may transition into the interictal phase.

A time lapse 116 is provided to skip to the next seizure occurring in EEG waveforms 102 and 104. The EEG waveform 106 indicates that the patient is still in the interictal phase and that a subsequent seizure has not occurred. The second seizure shown in the EEG waveform 102 ends at time 118 and shows normal recovery during the postictal phase. The second seizure shown in the EEG waveform 104 ends at time 118 and enters an EEG suppression period 120 that is longer than the previous EEG suppression period 112. The EEG waveform 106 transitions from an interictal phase at time 118 and enters an EEG suppression period 122 that is longer than the previous EEG suppression period 114 without any intervening seizures. This increase in the duration of the EEG suppression periods in the EEG waveforms 104 and 106 may be indicative of a progressive or worsening condition that may lead to a severe neurological event, such as SUDEP.

While FIG. 1 depicts one EEG signal for each of the scenarios, EEG readings are typically performed on many channels representing measurements from many EEG sensors. Whether one channel, two or more channels or all channels will be suppressed in a condition leading to SUDEP, or whether there will be a cascading effect, may depend on the particular pathology of the patient or the severity of the patient's current condition. One set of channels may exhibit a suppressive behavior pattern. The suppressive behavior pattern may migrate to another location or could propagate, with additional channels exhibiting the suppressive behavior. Often a higher number of channels being involved indicates that the case may be more serious.

By detecting a period of postictal EEG suppression, one may be able to intervene to assist the patient and prevent SUDEP. But any assistance must be prompt because potential remedies for SUDEP may not be effective unless they are applied in a timely manner. Possible treatments include activating an implanted medical device, such as a neurostimulator described in U.S. Pat. No. 5,304,206, an injection of an appropriate dosage of medicine, CPR and/or defibrillation, use of an external device, such as a helmet for cooling the brain, or EMS (electromagnetic stimulation). The treatment could be increased or changed if the patient does not respond. For example, the neurostimulator could include successive rounds of stimulation at higher currents if the postictal EEG suppression continues. Appropriate medication could be injected via a pump device, with an additional dose being added if the patient is not responsive. Depending on the patient and the treating physician's evaluation, more than one treatment may be used, either in combination or sequentially, for some patients.

Figure 2:
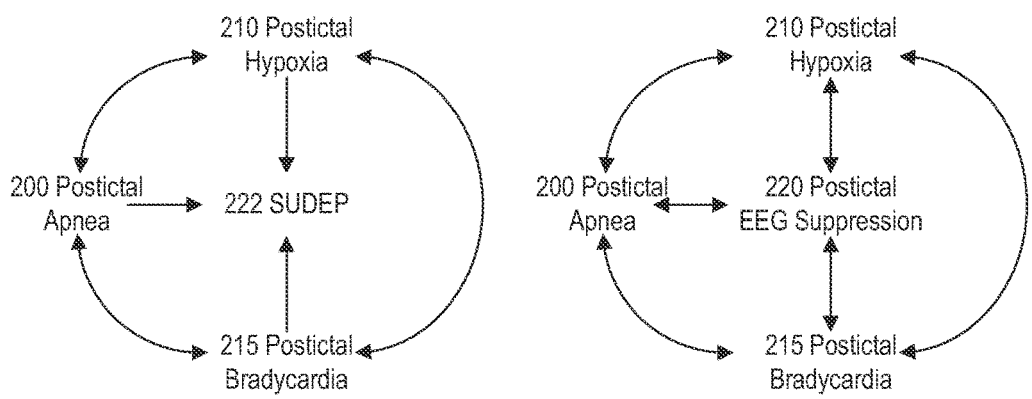
FIG. 2 is a depiction of relationships between some conditions that may be related to SUDEP.

FIG. 2 is a depiction of relationships between conditions that may be related to SUDEP 222 and to postictal EEG suppression 220. Conditions which may be related to SUDEP 222 and postictal EEG suppression 220 include postictal apnea 200, postictal hypoxia 210 and postictal bradycardia 215. Postictal apnea 200, which is an absence of breathing, can give rise to both postictal hypoxia 210, which is decreased levels of oxygen in a person, and postictal bradycardia 215, which is a slowing of a person's heart rate. Both postictal hypoxia 210 and postictal bradycardia 215 can in turn increase postictal apnea 200. Postictal hypoxia 210 can also increase postictal bradycardia 215. All of these conditions may also contribute to, or be indicative of, postictal EEG suppression 220 and may be present before, or during, SUDEP 222. This may explain why postictal EEG suppression 220 may also be indicative of SUDEP 222.

Figure 3A:
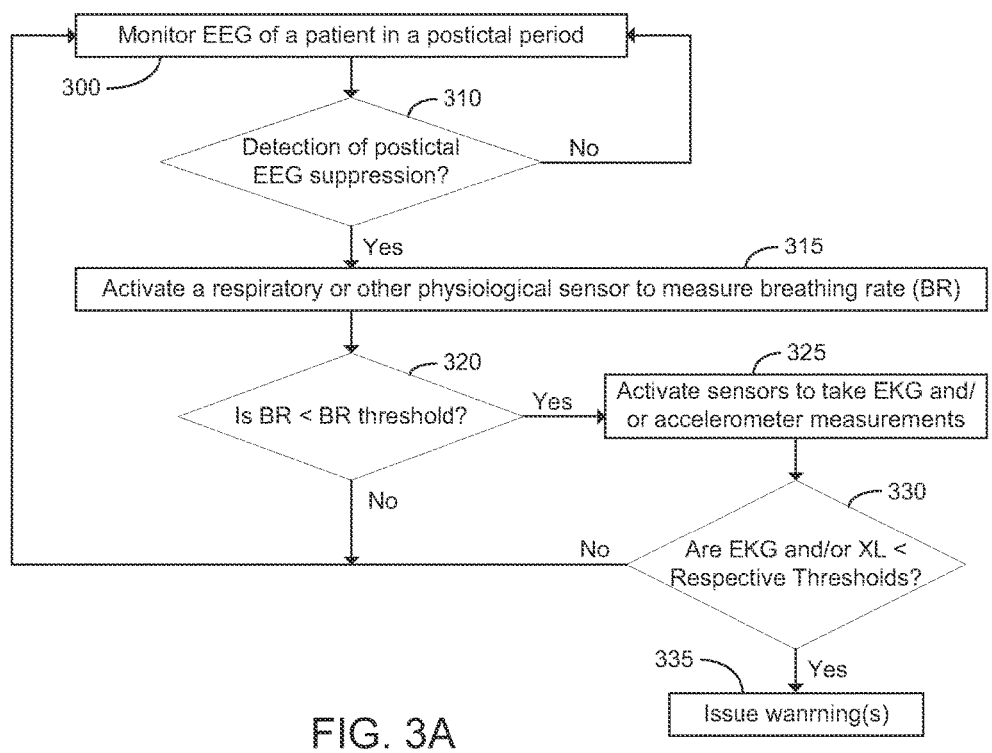

FIG. 3A is a depiction of a flowchart for a process in accordance with one or more embodiments of the present disclosure. A patient's EEG readings are monitored 300 during at least postictal portions of a seizure and preferably starting within the ictal period of the seizure. Many techniques could be used to detect an EEG suppression, such as a nonlinear signal analysis or a recurrence quantification analysis. The EEG suppression may last for a relatively long time or it may comprise shorter, re-occurring periods of suppression, interspersed with periods of normal activity. In the latter case, the re-occurring periods of suppression may progressively get worse. While an EEG suppression is most likely during the postictal phase, it may occur at other times as well. In several typical scenarios, the EEG suppression may occur 45-95 minutes after a seizure has occurred. Accordingly, in various embodiments of the disclosure, monitoring may occur outside of the postictal phase or may be continuous. The EEG suppression may be progressive exhibiting a trend of generally increasing duration of successive suppression periods. A single suppression period may occur after each seizure where each suppression period after each successive seizure generally increases in duration. Alternatively, multiple suppression periods may occur after a single seizure exhibiting the trend of generally increasing duration. The multiple suppression periods may be interleaved with non-suppression periods where the non-suppression periods exhibit a trend of generally decreasing duration.

If there is detection 310 of an EEG suppression, then a respiratory or other physiological sensor is activated 315 to measure breathing rate ("BR") of the patient. If the breathing rate falls 320 below a first predetermined threshold, such as a respiratory threshold, then EKG and/or accelerator measurements 325 may be taken 325 of the patient. If EKG readings are less than a second predetermined threshold 330, such as an EKG threshold, and/or accelerator measurements are less than 330 a third predetermined threshold, then a warning is issued 335 by a warning device. The warning can be audible, visual and/or vibrational. A warning device could also send messages, such as recorded telephone calls or e-mail messages or text messages to designated persons. The messages in one or more embodiments of the present disclosure may include information about measurements done on the patient. The warning may be local in nature, alerting the patient (if conscious) and/or those in immediate attendance upon the patient and/or may be sent to appropriate medical responders not in the immediate vicinity of the patient.

In other embodiments, the breathing rate and/or the EKG measurements may be monitored differently, such as continuously or while EEG measurements are taken.

FIG. 3B is a depiction of one embodiment of a method for detecting a condition in a patient that poses an increased risk of a severe neurological event, such as sudden unexplained death in epilepsy (SUDEP). The method collects EEG data from a patient during at least a postictal phase of one or more seizures at 340. The method further determines whether the EEG data indicates postictal EEG suppression when the EEG data crosses an EEG threshold, at 345, where the postictal EEG suppression is progressive postictal EEG suppression comprised of multiple suppression periods interleaved with non-suppression periods. The postictal EEG suppression may be progressive when the suppression is characterized by a trend of generally increasing duration with time of the multiple suppression periods. The method further activates a warning device when the EEG data indicates postictal EEG suppression for a predetermined period of time at 350.

FIG. 3C is a depiction of another embodiment of a method for detecting a condition in a patient that poses an increased risk of a severe neurological event, such as sudden unexplained death in epilepsy (SUDEP). The method collects EEG data from a patient during at least a postictal phase of one or more seizures, at 355, and determines whether the EEG data indicates postictal EEG suppression when the EEG data crosses an EEG threshold, at 360. The method further collects respiratory data from the patient's respiration, at 365, and determines whether the respiratory data crosses a first threshold, at 370. The method further collects EKG data for the patient's heart, at 375, and determines whether the EKG data crosses a second threshold, at 380. The method activates a warning device when the EEG data indicates postictal EEG suppression for a predetermined period of time, the respiratory data crosses the first threshold, and the EKG data crosses the second threshold, at 385.

Figure 4:
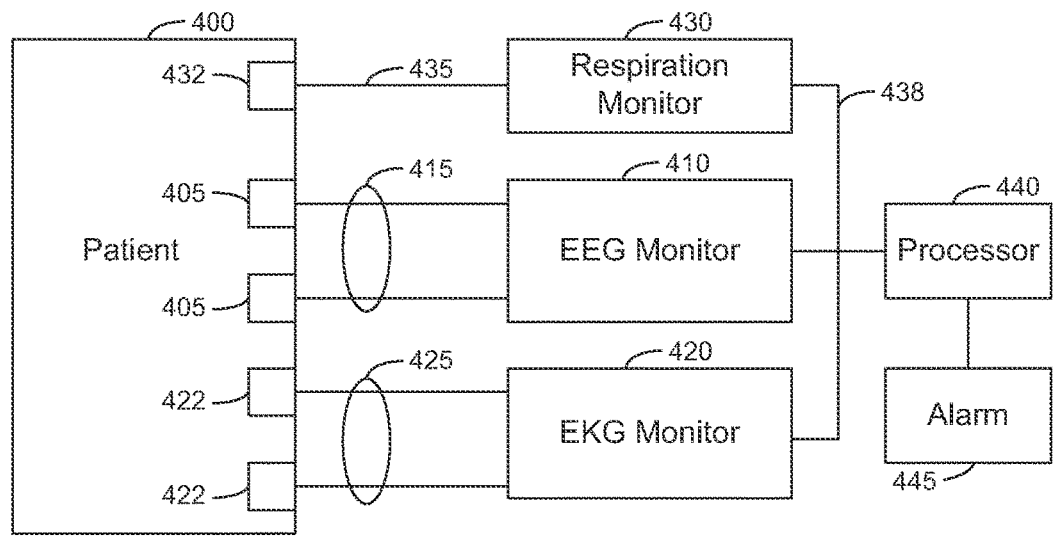
FIG. 4 is a depiction of a system for a patient in a medical facility in accordance with one or more embodiments of the present disclosure.

FIG. 4 is a depiction of a system for a patient in a medical facility or at home, for use during sleep, for example, in accordance with one or more embodiments of the present disclosure. A patient 400, who may be asleep or between seizures or in an ictal or postictal portion of a seizure, has EEG sensors 405 placed on the patient's body in appropriate locations for taking EEG measurements. The EEG sensors 405 are attached to an EEG monitoring unit 410, via an EEG lead 415. Although two EEG sensors 405 and EEG leads 415 are depicted in FIG. 4, there may be many EEG sensors 405 and EEG leads 415. Although EEG leads 415 are currently used for transmitting information from the EEG sensors 405 to the EEG monitoring unit 410, it may be practical in the future to transmit information from the EEG sensors 405 to the EEG monitoring unit 410 wirelessly. Wearable EEG monitors for personal or home use are becoming available commercially. (See e.g. the HealthPals™ device by Olga Epikhina.)

In alternate embodiments, an EEG helmet or headgear may be used and may include many sensors. Alternatively, in the absence of EEG data or in addition thereto, heart and respiration measurements may be used as surrogate markers. For example, during EEG suppression, respiration may proceed in a pattern from tachycardia, to bradycardia, and back to tachycardia.

In the embodiment depicted in FIG. 4, the patient 400 is also monitored by an EKG monitoring unit 420 having EKG sensors 422 placed on the patient's body to monitor the patient's heart activity and linked to the EKG monitoring unit 420 through one or more EKG leads 425. Although two EKG sensors 422 and EKG leads 425 are depicted in FIG. 4, there may be many EKG sensors 422 and EKG leads 425. While EKG's have traditionally been used in a hospital setting, handheld EKG's for home use are now commercially available, some with only a single EKG sensor 422. Although EKG leads 425 are currently used for transmitting information from the EKG sensors 422 to the EKG monitoring unit 420, it may be practical in the future to transmit information from the EKG sensors 422 to the EKG monitoring unit 420 wirelessly.

Continuing to refer to FIG. 4, in this embodiment of the present disclosure, the respiration of the patient 400 is also monitored through a respiratory monitoring unit 430, which includes one or more respiratory sensors 432 attached to the patient's body 400 through one or more respiratory leads 435. Respiration may be monitored in many ways, for example, by use of a nose clip, by a chest band to determine chest expansion, by measuring the temperature of the inhale versus the temperature of the exhale, indirectly by use of an oximeter, or by impedance measurements using chest electrodes. There are some caveats to using respiration measurements in embodiments of the disclosure, but a treating physician can evaluate these factors in determining how to treat a specific patient. For example, respiration could be subject to natural cycles and certain conditions, such as obstructive sleep apnea or central sleep apnea, may mimic SUDEP conditions, resulting in a false SUDEP warning. But considered carefully, respiration measurements may be helpful in different embodiments of the present disclosure.

Signals from the EEG monitoring unit, the EKG monitor unit and the respiratory monitoring unit are fed through one or more signal lines 438 to a processor 440 (or processing unit). Alternatively, the signals could be sent to the processor 440 in a wireless fashion. The processor 440 runs software preferably capable of determining three conditions, including whether: (1) the EEG measurements indicate a period of postictal suppression; (2) the respiration of the patient has fallen below a first threshold and (3) the EKG measurements have fallen below a second threshold. If all three conditions are met, the processor 440 activates an alarm 445, signaling the need for immediate medical intervention. In alternative embodiments, the processor 440 is set so that it signals the alarm if two of the three conditions are met. For example, if EEG measurements are not available or show no change, but heart rate cycles and respiration cycles become longer, more progressive and more extreme, a warning should be triggered.

In some cases, the alarm may be triggered if just one of the conditions is met or if the EEG suppression is prolonged, even if the other two conditions are not met. The EEG suppression is typically the most specific and earliest marker, and in some embodiments of the present disclosure, detection of EEG suppression may alone trigger the alarm. Severe or progressive deterioration of respiration or heart rate may also warrant alarm activation in some patients.

In alternative embodiments, different alarms or messages may be activated for each of the different kinds of measurements being taken of a patient. In alternative embodiments, other physiological measurements with related thresholds may be substituted for the respiratory measurements and the EKG measurements.

Figure 5:
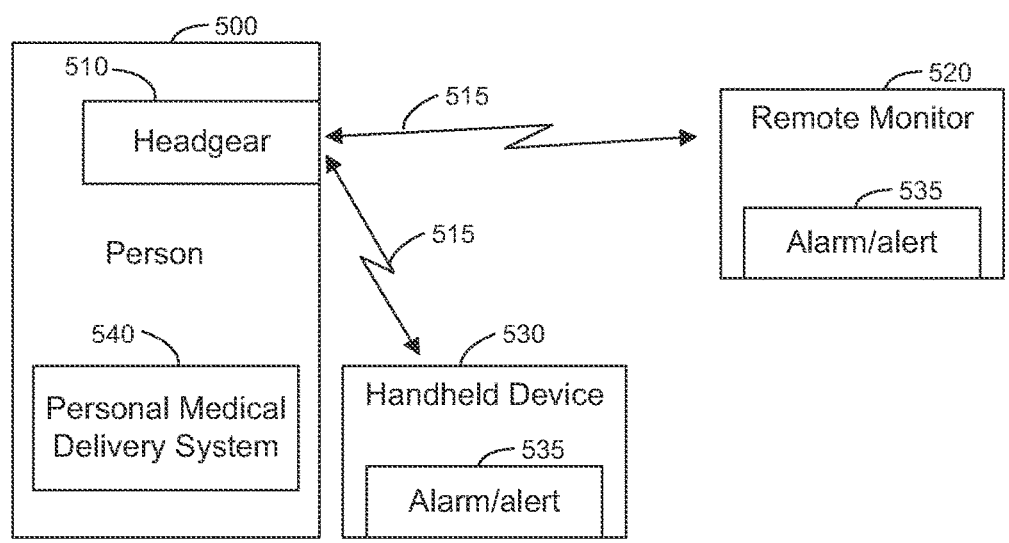
FIG. 5 is a depiction of a system for a patient outside of a medical facility, in accordance with one or more embodiments of the present disclosure.

FIG. 5 is a depiction of a system for a patient outside of a medical facility, in accordance with one or more embodiments of the present disclosure. In FIG. 5, a person 500 is wearing a headgear 510 containing one or more sensors, which take EEG measurements of the person 500, preferably on a real time basis. The EEG measurements are sent, preferably wirelessly 515, but alternatively through wired connections, to a one or more EEG monitoring units 520, 530, which may include a remote monitor 520 and/or a local monitor 530, such as a handheld device 530, either or both of which can store and analyze the EEG measurements. Should the person's 500 EEG measurements fall below a predetermined threshold, such as an EEG threshold, alarms or alerts 535 are executed by the handheld device 530 and the remote monitor 520. The EEG threshold may include falling below a level of brain activity for a predetermined time period. Additional alerts 535 could be sent to specified recipients such as medical responders and/or family members and/or other designated persons. The person's location could also be provided to the recipients using a GPS or other locator which might be a function included with the handheld device 530 or provided on a separate device in communication with the handheld device 530.

Continuing to refer to FIG. 5, should no help arrive within a pre-determined period of time and/or the person's EEG measurements remain suppressed during the predetermined period of time, an optional personal medical delivery system 540 could automatically introduce an emergency remedy into the patient's system in an attempt to avert imminent death. The personal medical delivery system 540 could, for example, comprise a neurostimulator, such as that described in U.S. Pat. No. 5,304,206, or an implantable medical device for delivery of a premeasured dosage of medicine, a brain cooling system, CPR and/or defibrillation or EMS (electromagnetic stimulation). The headgear 510 could continue to monitor the patient's condition, with successive or alternative therapy being delivered by the optional personal medical delivery system 540 as needed, until and unless deactivated by medical personnel.

In one or more embodiments of the disclosure, the alert device could also provide written or verbal instructions to those attending to the person. The processor of the present disclosure could maintain a record of measurements made by the system for display, downloading or transmittal to other sites.

In light of the principles and example embodiments described and illustrated herein, it will be recognized that the example embodiments can be modified in arrangement and detail without departing from such principles. Also, the foregoing discussion has focused on particular embodiments, but other configurations are contemplated. In particular, even though expressions such as "in one embodiment," "in another embodiment," or the like are used herein, these phrases are meant to generally reference embodiment possibilities, and are not intended to limit the disclosure to particular embodiment configurations. As used herein, these terms may reference the same or different embodiments that are combinable into other embodiments.

Similarly, although example processes have been described with regard to particular operations performed in a particular sequence, numerous modifications could be applied to those processes to derive numerous alternative embodiments of the present invention. For example, alternative embodiments may include processes that use fewer than all of the disclosed operations, processes that use additional operations, and processes in which the individual operations disclosed herein are combined, subdivided, rearranged, or otherwise altered.

This disclosure also described various benefits and advantages that may be provided by various embodiments. One, some, all, or different benefits or advantages may be provided by different embodiments.

In view of the wide variety of useful permutations that may be readily derived from the example embodiments described herein, this detailed description is intended to be illustrative only, and should not be taken as limiting the scope of the invention. What is claimed as the invention, therefore, are all implementations that come within the scope of the following claims, and all equivalents to such implementations.

What is claimed is:

1. A system for identification of an increased risk of a severe neurological event, comprising:
   an electroencephalogram (EEG) monitoring unit configured to receive EEG data generated by one or more EEG sensors adapted to sense neurological activity of a patient during at least a postictal phase of each of one or more seizures; and
   a processing unit configured to:
      receive the EEG data from the EEG monitoring unit;
      detect a plurality of postictal EEG suppression periods interleaved with postictal EEG non-suppression periods during each of at least one postictal phase of the one or more seizures from the EEG data, wherein a postictal EEG suppression period is detected when the EEG data crosses an EEG threshold for at least a predetermined time period;
      detect a first trend of generally increasing duration with time of the plurality of postictal EEG suppression periods during the postictal phase of one or more seizures; and
      identify the increased risk of the severe neurological event based on the first trend.

2. The system of claim 1, wherein the severe neurological event is sudden unexplained death in epilepsy (SUDEP).

3. The system of claim 1, wherein at least a first EEG suppression period of the plurality of postictal EEG suppression periods occurs after a first seizure and at least a second EEG suppression period of the plurality of postictal EEG suppression periods occurs after a second seizure, the second seizure occurring after the first seizure.

4. The system of claim 1, wherein a progressive postictal EEG suppression is characterized by the first trend, and wherein the progressive postictal EEG suppression is further characterized by a second trend of generally decreasing duration with time of the plurality of postictal EEG non-suppression periods during the postictal phase of the one or more seizures.

5. The system of claim 1, further comprising:
   a respiratory monitoring unit configured to collect respiratory data from the patient, wherein the processing unit is configured to receive the respiratory data from the respiratory monitoring unit and to determine whether a breathing rate determined from the respiratory data crosses a respiration threshold.

6. The system of claim 5, wherein the processing unit is configured to determine whether the breathing rate crosses the respiration threshold in response to a determination that the EEG data crosses the EEG threshold.

7. The system of claim 5, further comprising:
   an electrocardiogram (EKG) monitoring unit configured to collect EKG data from the patient, wherein the processing unit is configured to receive the EKG data from the EKG monitoring unit and to determine whether the EKG data crosses an EKG threshold.

8. The system of claim 7, wherein the processing unit is configured to determine whether the EKG data crosses the EKG threshold in response to a determination that the breathing rate crosses the respiration threshold.

9. A method for detecting a condition in a patient that poses an increased risk of sudden unexplained death in epilepsy (SUDEP), the method comprising:
   collecting, at a processor of a medical device, electroencephalogram (EEG) data from one or more EEG sensors adapted to sense neurological activity of a patient during at least a postictal phase of each of one or more seizures;
   determining, via the processor, that the EEG data indicates postictal EEG suppression when the EEG data crosses an EEG threshold for at least a predetermined time period;
   detecting, via the processor, a plurality of postictal EEG suppression periods interleaved with postictal EEG non-suppression periods during each of at least one postictal phase of the one or more seizures from the EEG data;
   detecting, via the processor, a first trend of generally increasing duration with time of the plurality of postictal EEG suppression periods during the postictal phase of one or more seizures; and
   identifying, via the processor, the increased risk of the severe neurological event based on the first trend.

10. The method of claim 9, wherein the predetermined time period is a first predetermined time period, the method further comprising:
   activating a warning device when the EEG data indicates postictal EEG suppression for a second predetermined period of time.

11. The method of claim 9, further comprising:
collecting respiratory data from the patient;
determining whether a breathing rate determined from the respiratory data crosses a first threshold;
collecting electrocardiogram (EKG) data patient; and
determining whether the EKG data crosses a second threshold.

12. The method of claim 11, wherein the predetermined time period is a first predetermined time period, the method further comprising:
activating a warning device when the EEG data indicates postictal EEG suppression for a second predetermined period of time, the breathing rate crosses the first threshold, and the EKG data crosses the second threshold.

13. The method of claim 9, wherein the postictal EEG suppression is progressive postictal EEG suppression comprised of multiple suppression periods interleaved with non-suppression periods.

* * * * *